United States Patent [19]
Dan

[11] Patent Number: 5,956,124
[45] Date of Patent: Sep. 21, 1999

[54] AUTOMATED THRESHOLD-RELATED OBJECTIVE PERIMETRY

[76] Inventor: Jacob Dan, 22 Dvorah Street, Hod Hasharon, Israel

[21] Appl. No.: 08/956,433

[22] Filed: Oct. 23, 1997

[51] Int. Cl.$^6$ ..................................................... A61B 3/10
[52] U.S. Cl. ........................... 351/221; 351/205; 351/210
[58] Field of Search ................................... 351/221, 211, 351/205, 200, 246, 247, 212, 204, 222, 223, 224, 210, 209

[56] References Cited

U.S. PATENT DOCUMENTS 5,530,495 6/1996 Lamprecht ............................... 351/210

*Primary Examiner*—Hung Xuan Dang
*Attorney, Agent, or Firm*—Mark M. Friedman

[57] ABSTRACT

A system for an examination of an eye of a patient, the system including: (a) a head set attached to the head of the patient; (b) a screen attached to the head set, such that the eye of the patient is covered by the screen; (c) a plurality of light sources attached to the screen, such that light is projected from at least one of the light sources directly to a preselected area of the retina of the eye of the patient to form reflected light; (d) a light receiving device attached to the head set to receive the reflected light and to transmit a signal according to the received reflected light; (e) an eye tracking device to determine the position of the eye relative to the light receiving device; and (f) a microprocessor for receiving the signal and for analyzing the signal to determine a size of a pupil of the eye and an amount of light reflected from the retina of the eye, such that a pupillary light response is measured to perform the examination. Also provided is a method for using the system of the present invention to perform an examination of the visual field of an eye of the patient. Preferably, the light receiving device is also able to continuously track, or follow, the position of the eye relative to the light receiving device. The method of examination preferably includes the steps of tracking the position of the eye, stimulating a preselected area of the retina with light at a retinal threshold intensity and then measuring both pupillary size and the amount of reflected light in order to determine the field of vision of the patient.

9 Claims, 2 Drawing Sheets

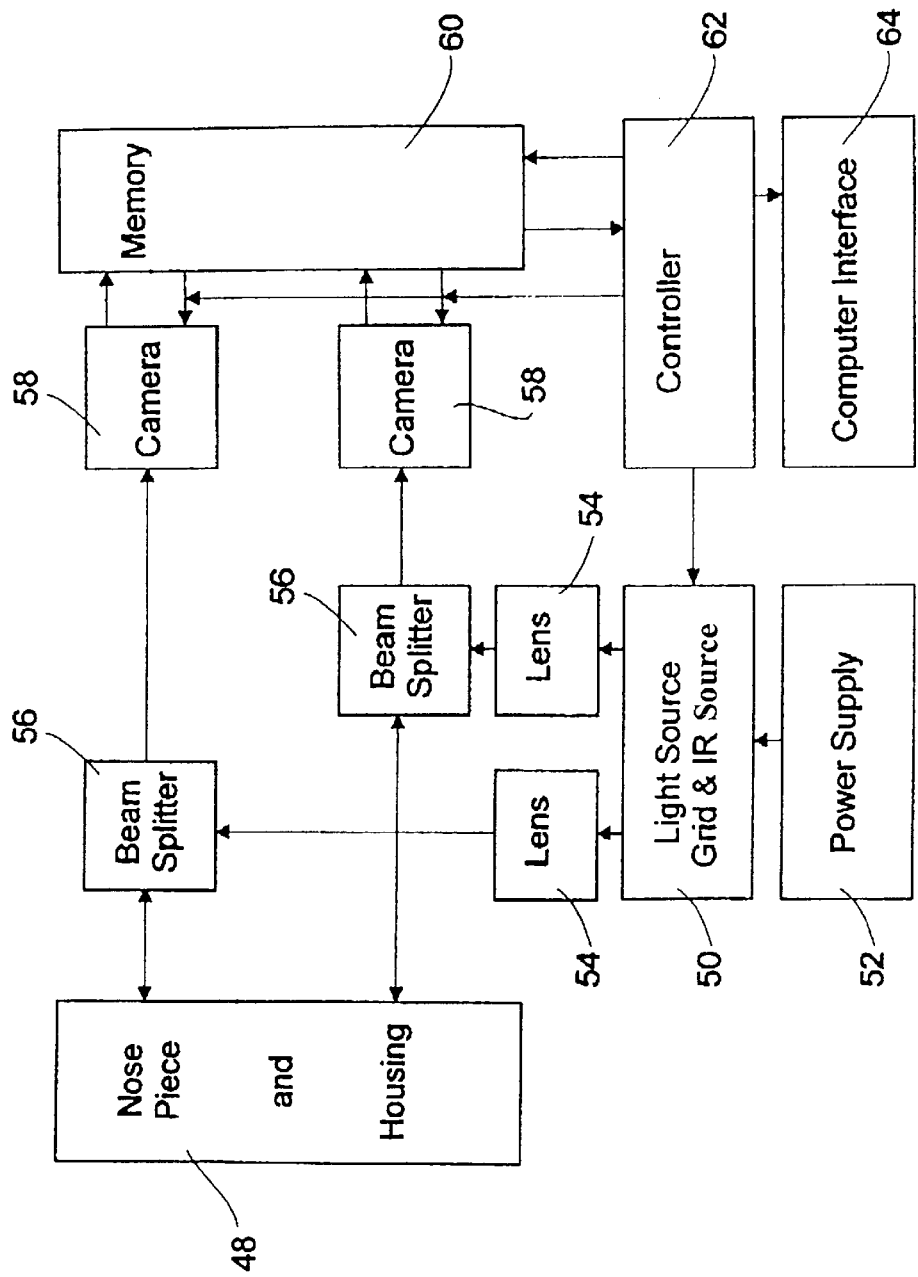
Fig. 2 Sensor Block Diagram

AUTOMATED THRESHOLD-RELATED OBJECTIVE PERIMETRY

FIELD AND BACKGROUND OF THE INVENTION

The present invention is concerned with methods and equipment for diagnostic tests of the eyes, and more particularly, with an automatic system for examination of the field of vision of a patient. The system is mounted on a head set and is equipped to continuously track eye movement so as to focally project a spot of retinal threshold-related light stimuli on preselected retinal areas, regardless of the direction of the gaze of the patient or of the orientation of the head of the patient. The system can concomitantly measure the pupil size and intensity of light reflected through the pupil as a result of the light projected.

The examination of the field of vision of a patient is an extremely important diagnostic tool used to identify and analyze diseases and defects of the retina and as visual pathways, such as glaucoma, optic neuropathy, multiple sclerosis and compression of the visual pathways. In the past, such an examination was performed with manually operated field of vision test instruments known as perimeters. Manually operated perimeters require the services of a physician or a skilled technician in order to examine the patient. In the most widely used system, known as the Goldmann system, the patient must sit still, head clamped in place, and constantly watch a fixation target at the center of a hemispherical screen to eliminate any uncertainties caused by head and eyes movements. A small point of light of varied intensity, size and color is projected onto the screen and its position is varied by the operator. The limits of the visual field are determined on the basis of the manual or verbal indications of the patient as to when the point of light comes into or goes out of view as the light is moved radially between the periphery and the center of his view. The examiner must continuously watch the patient to ascertain that the eye of the patient is fixated on the center of the screens since the examination results are artefactual if the eyes of the patient are not immobile. These factors render the examination of the extent of the field of vision using the commonly available Goldmann system is basically subjective, dependent to a large extent on the skill of the examiner, the fatigue level of the patient and the ability of the examiner to communicate with the patient. Thus, the Goldmann system is not operable for small children and patients who must remain in a supine position.

More recently, automatic perimeters have been marketed and used. However, even these instruments rely upon the Goldmann system and incorporate the control of a microprocessor in order to more efficiently measure the effect of light stimuli from external sources. Other prior art instruments have added a head set or helmet to eliminate any effect of head movements on the final results, as disclosed in United Kingdom Application No. 2096791 and two reports from the IOVS [J. Whiteside-Michel et al., "Virtual Reality Visual Field Test.", IOVS/97, 38:4, S569; and L. Brigatti et al., "Virtual Perimetry: A Novel Perinmetric Technique", IOVS/97, 38:4, S572]. Alternatively, various systems have been disclosed which use more objective means for perimetry such as pupillary size determination during Humfrey perimetry, as disclosed in U.S. Pat. No. 5,490,098. U.S. Pat. No. 5,114,222 discloses a method which includes a light stimulus moved in a continuous circular path according to decreased pupillary response. U.S. Pat. No. 5,459,536 discloses an instrument which includes a device to track eye movement, so that such movements can be incorporated into the final analysis of the results. However, all of these instruments and methods perform indirect measurements in which the light stimulus is projected in front of the eyes of the patient, rather than directly stimulating the retinal nerve fibers with fight.

There is thus an unmet medical need for a method and a system which objectively examines the visual field of a patient in which the retinal nerve fibers are directly stimulated by a retinal threshold-related light stimulus, such that the change in pupillary size in response to this light is automatically measured, and such that this measurement is cross-checked by determination of the change in the amount of light reflected from the retina, such that the patient does not need to remain substantially immobile during the examination and such that the method and system can be used to examine patients which must remain supine or who cannot otherwise comply with the requirements of prior art manual perimetry methods.

SUMMARY OF THE INVENTION

According to the present invention, there is provided a system for an examination of an eye of a patient, the system including: (a) a head set attached to the head of the patient; (b) a screen attached to the head set, such that the eye of the patient is covered by the screen; (c) a plurality of light sources attached to the screen, such that light is projected from at least one of the light sources directly to a retina of the eye of the patient to form reflected light; (d) a light receiving device attached to the head set to receive the reflected light and to transmit a signal according to the received reflected light; and (e) a microprocessor for receiving the signal and for analyzing the signal to determine a size of a pupil of the eye and an amount of light reflected from the retina of the eye, such that a pupillary light response is measured to perform the examination.

Preferably, the light receiving device also collects a visual image of the pupil, the visual image indicating an apparent shape of the pupil, such that a location of the pupil and a position of the eye relative to the light receiving device is determinable from the apparent shape. More preferably, the light sources are in a form of a dense grid, such that a particular light source is able to illuminate a specific area of the retina. Most preferably, the microprocessor transmits a return signal to the light sources, such that the particular light source is selected according to the location of the pupil in order to illuminate the specific area of the retina. Also most preferably, an characteristic of light projected by the at least one light source is determined according to the return signal, the characteristic being selected from the group consisting of an intensity and a wavelength of the light.

According to other preferred embodiments of the present invention, the light source is of a type selected from the group consisting of halogen lamp, mercury arc lamp and LED. Preferably, the halogen lamp and the mercury arc lamp feature a plurality of optic fibers for focusing the emitted light on the retina of the eye.

According to another embodiment of the present invention, there is provided a method for determining a visual field of an eye of a patient, the method comprising the steps of: (a) providing an instrument for determining the visual field, the instrument featuring: (i) a head set attached to the head of the patient; (ii) a screen attached to the head set, such that the eye of the patient is covered; (iii) a plurality of light sources attached to the screen; (iv) an eye tracking device; (v) a light receiving device attached to the head set;

and (vi) a microprocessor; (b) continuously following a position of the eye relative to the light receiving device; (c) projecting light from at least one of the light sources directly onto a preselected area of a retina of the eye; (d) measuring an amount of reflected light from the retina and capturing a visual image of a pupil of the eye with the light receiving device; (e) calculating a pupillary light response from the amount of reflected light and from the visual image of the pupil with the microprocessor; and (f) determining the visual field of the eye from the pupillary light response.

Hereinafter, the term "patient" refers to any subject, particularly a human or higher mammal, capable of being examined with the system of the present invention.

BRIEF DESCRIPTION OF THE DRAWINGS

The invention is herein described, by way of example only, with reference to the accompanying drawings, wherein:

FIG. 2 is a sensor block diagram of the present invention.

DESCRIPTION OF THE PREFERRED EMBODIMENTS

Figure 1:
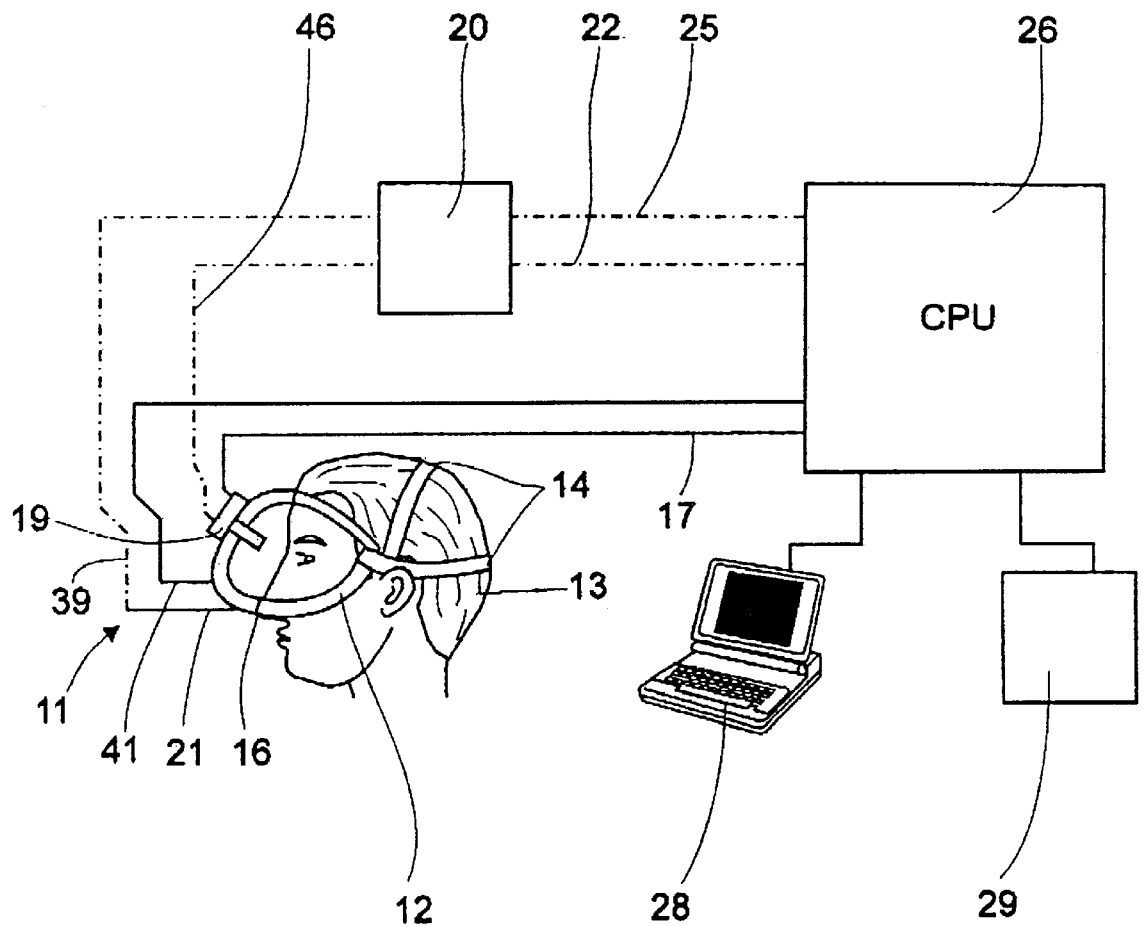
FIG. 1 is an illustration of the system of the present invention.

The present invention is of an automatic perimetry system, including an instrument for automated perimetry measurements and a method for operating the instrument. The system includes a headset to be placed on the head of a patient. The headset supports a screen for background illumination; an eye tracking device; a plurality of light sources for focal retinal stimulation; and two light receiving devices, one for each eye. The light sources are preferably capable of emitting light of an adjustable intensity, such that the intensity of the light matches the threshold of the retina to light stimuli. Preferably, each light receiving device is able to follow the position of the eye, to measure the amount of light reflected from the retina, and to visually capture an image of the pupil itself. Thus, the eye tracking device is preferably incorporated within the light receiving device.

The output of the light receiving devices, in terms of both the amount of light reflected from the retina and the image of the pupil, is sent to a microprocessor. From this output, the microprocessor continuously calculates both the resulting pupillary area and the correct amount of reflected light to determine the pupillary light response. Preferably, the microprocessor incorporates information about the position of the eye relative both to the particular active light source and to the light receiving device, such that even if the eye moves, the pupillary light response can be accurately determined. The position of the pupil relative to the light receiving device and the light sources can be determined from the visual image of the pupil. When the pupil is viewed straight on, the pupil appears to be round. If the eye moves so that the pupil is now viewed at an angle, the shape of the pupil appears to change to an oval. Thus, the microprocessor, or more accurately the software instructions performed by the microprocessor, is able to determine the position of the pupil from the visual image.

The microprocessor also directs the light emission from the different light sources to preselected loci on the retina of the eye of the subject, according to the above analysis of the output of the light receiving devices. For example, in order to stimulate one particular area of the retina, the microprocessor must select one particular light source which is focused on that area. In order to determine which light source should be selected, the microprocessor preferably first determines the position of the eye, and hence of the retina, relative to the plurality of light sources. Next, the particular light source which can stimulate the desired retinal area at that moment is selected. The output of the light receiving device is then analyzed as described previously.

Since both the light emission source and the light receiving devices are attached to the headset; the pupil size, amount of reflected light and eye movement can be continuously monitored. Such continuous monitoring permits consensual pupillary monitoring whereby movement of the head and eyes of the patient during perimetry testing does not affect the test results, thus objectively measuring the visual field by automatic determination of the pupillary light response.

The principles and operation of a system according to the present invention may be better understood with reference to the drawing and the accompanying description.

Referring now to the drawing, FIG. 1 illustrates the automatic perimetry system of the present invention. A system 11 includes a head set 12, in a view partially cut away to show the interior. Head set 12 is attached to the head 13 of a patient, preferably by straps 14. Head set 12 preferably has an oval shape with a hemispherical construction covering the eyes and the upper part of the face of the patient. Such a construction enables a hemispherical screen 16 to be placed within head set 12. A plurality of light sources 19 are attached to hemispherical screen 16. Preferably, hemispherical screen 16 is very close to the eyes of the patient, even as close as about 2 cm. Also preferably, light sources 19 substantially cover the surface of hemispherical screen 16 in the form of a dense grid, for example. Such a grid enables a particular light source 19 to be selected for emitting light in a highly focused manner. Also, such a grid eliminates the need for any mechanical movement of light sources 19 in order to focus on a particular portion of the retina, since simply illuminating one particular tight source 19 would stimulate only one specific area of the retina, automatically giving focus to the emitted light.

Light sources 19 are preferably in the form of a LED, in which the light is generated by a power supply device 20 also attached to head set 12, more preferably mounted on the outer periphery of head set 12. Alternatively and preferably, light could be generated by a halogen lamp or a mercury arc lamp connected to power supply device 20 and then directed to the retina by a bundle of fiber optics, the end of each fiber forming a point on the dense grid. In any case, light is focused on a specific area of the retina regardless of any movements of the head or eyes of the patient for a number of reasons. First, light sources 19 are directly attached to head set 12 so that light sources 19 move with the movements of the patient. Second, in the preferred embodiment of a dense grid of light sources 19, a specific area of the retina is illuminated by the emission of light from one particular light source 19. These features enable the emitted light to be correctly reflected from the retina of the patient.

Once light is reflected from the retina of the eye of the patient, the reflected light is detected by a light receiving device 21 mounted in the inner periphery of head set 12. Light receiving device 21 is preferably supplied with energy by power supply device 20. Light receiving device 21 preferably is a CCD camera, although alternatively light receiving device 21 could be at least one photomultiplier tube. A CCD camera is more preferable because such a camera is capable of continuous video monitoring of the pupil, including both the capture of a visual image of the pupil and the measurement of the amount of light reflected from the retina. Such information can be used to determine the position of the eye relative to the horizontal and vertical axes, as well as to cross-check the eye position by using the Hirshberg corneal reflex. Thus, light receiving device 21 preferably collects a visual image of the pupil and the amount of light reflected from the retina, and then transmits this information in the form of signals.

These signals obtained by light receiving device 21 are then transmitted through a communication link such as a cable 41 to a microprocessor 26. Microprocessor 26 operates software (not shown), which permits the analysis of the received data to determine the measured pupillary light response. In particular, the software preferably first analyzes the visual image of the pupil in order to determine the location of the pupil relative to both the particular light source 19 which was illuminated and to light receiving device 21. As noted previously, such an analysis could include the determination of the apparent shape of the pupil from the visual image which gives information about the position of the pupil relative to light receiving device 21, and hence to light source 19. Next, the software determines the size of the pupil both directly from the visual image and also from the amount of light reflected from the retina, which is determined by the size of the pupil. Finally, all of this information is analyzed to determine if the response to stimulation of a particular area of the retina was normal or abnormal.

The software also uses the analysis to enable microprocessor 26 to send return signals to light sources 21, causing the right intensity of light to be generated by the desired light source 21, such that light is projected to an area of the retina selected by the software in order to more accurately assess the field of vision. Each area of the retina can thus be examined separately, regardless of the movement of the eye or the position of the pupil, without any voluntary activity on the part of the patient.

Preferably, microprocessor 26 is able to connect and download the data into a computer or alternatively directly to a printer. According to other preferred embodiments, microprocessor 26 also controls the wavelength of light emitted by light sources 19. Such control could permit additional types of ocular examinations to be performed with system 11.

While the invention has been described with respect to a limited number of embodiments, it will be appreciated that many variations, modifications and other applications of the invention may be made.

What is claimed is:

1. A system for an examination of an eye of a patient, the system comprising:
   (a) a head set attached to the head of the patient;
   (b) a screen attached to said head set, such that the eye of the patient is covered by said screen;
   (c) a plurality of light sources attached to said screen, such that light is projected from at least one of said light sources directly to a retina of the eye of the patient to form reflected light;
   (d) a light receiving device attached to said head set to receive said reflected light and to transmit a signal according to said received reflected light; and
   (e) a microprocessor for receiving said signal and for analyzing said signal to determine a size of a pupil of the eye and an amount of light reflected from said retina of the eye, such that a pupillary light response is measured to perform the examination.

2. The system of claim 1, wherein said light receiving device also collects a visual image of said pupil, said visual image indicating an apparent shape of said pupil, such that a location of said pupil and a position of the eye relative to said light receiving device is determinable from said apparent shape.

3. The system of claim 2, wherein said light sources are in a form of a dense grid, such that a particular light source is able to illuminate a specific area of said retina.

4. The system of claim 3, wherein said microprocessor transmits a return signal to said light sources, such that said particular light source is selected according to said location of said pupil in order to illuminate said specific area of said retina.

5. The system of claim 4, wherein an characteristic of light projected by said at least one light source is determined according to said return signal, said characteristic being selected from the group consisting of an intensity and a wavelength of said light.

6. The system of claim 1, wherein said light source is of a type selected from the group consisting of halogen lamp, mercury arc lamp and LED.

7. The system of claim 6, wherein said mercury arc lamp features a plurality of optic fibers for focusing said emitted light on said retina of the eye.

8. The system of claim 6, wherein said halogen lamp features a plurality of optic fibers for focusing said emitted light on said retina of the eye.

9. A method for determining a visual field of an eye of a patient, the method comprising the steps of:
   (a) providing an instrument for determining the visual field, the instrument featuring:
      (i) a head set attached to the head of the patient;
      (ii) a screen attached to said head set, such that the eye of the patient is covered;
      (iii) a plurality of light sources attached to said screen;
      (iv) an eye tracking device attached to said head set;
      (v) a light receiving device attached to said head set; and
      (vi) a microprocessor;
   (b) continuously following a position of the eye with said eye tracking device;
   (c) projecting light from at least one of said light sources directly onto a preselected area of a retina of the eye, said light being at a retinal threshold intensity;
   (d) measuring an amount of reflected light from said retina and capturing a visual image of a pupil of the eye with said light receiving device;
   (e) calculating a pupillary light response from said amount of reflected light according to said position of the eye and from said visual image of said pupil with said microprocessor; and
   (f) determining the visual field of the eye from said pupillary light response.

* * * * *